(12) United States Patent
MacDougall

(10) Patent No.: US 11,911,630 B1
(45) Date of Patent: Feb. 27, 2024

(54) SMALL PROFILE LIGHT THERAPY PROBE

(71) Applicant: Lumeda inc, Rocky Hill, CT (US)

(72) Inventor: Trevor MacDougall, South Dartmouth, MA (US)

(73) Assignee: Lumeda Inc., Rocky Hill, CT (US)

( * ) Notice: Subject to any disclaimer, the term of this patent is extended or adjusted under 35 U.S.C. 154(b) by 0 days.

(21) Appl. No.: 18/005,626

(22) PCT Filed: Aug. 13, 2022

(86) PCT No.: PCT/US2022/040271
§ 371 (c)(1),
(2) Date: Jan. 16, 2023

(51) Int. Cl.
*A61N 5/06* (2006.01)
*A61N 5/067* (2006.01)

(52) U.S. Cl.
CPC .......... *A61N 5/062* (2013.01); *A61N 5/0601* (2013.01); *A61N 5/067* (2021.08); *A61N 2005/063* (2013.01); *A61N 2005/0628* (2013.01); *A61N 2005/0663* (2013.01); *A61N 2005/0664* (2013.01)

(58) Field of Classification Search
CPC ........ A61N 5/06; A61N 5/0601; A61N 5/062; A61N 2005/0628; A61N 2005/063; A61N 2005/0664; A61N 5/067
USPC ................................................ 607/88–90, 92
See application file for complete search history.

(56) References Cited

U.S. PATENT DOCUMENTS

| | | | | |
|---|---|---|---|---|
| 5,861,020 A * | 1/1999 | Schwarzmaier | ..... | A61N 5/0601 607/93 |
| 6,224,590 B1 * | 5/2001 | Daikuzono | .......... | A61N 5/0601 606/17 |
| 8,109,981 B2 * | 2/2012 | Gertner | ................ | A61N 5/0603 607/92 |
| 8,597,338 B2 * | 12/2013 | Carpentier | ............. | A61B 18/02 600/544 |
| 2006/0276699 A1 * | 12/2006 | Komachi | ............. | A61B 5/0075 600/341 |
| 2021/0251677 A1 | 8/2021 | Burnett | | |
| 2021/0318494 A1 * | 10/2021 | Schultheis | .............. | C03C 3/089 |

* cited by examiner

*Primary Examiner* — Ahmed M Farah
(74) *Attorney, Agent, or Firm* — Matthew J Patterson

(57) ABSTRACT

In some implementations, a PDT system may include a probe assembly having an elongated cylinder having a probe inner diameter and a probe outer diameter optical surface and a probe tip positioned on a distal end, a therapy window positioned proximal the probe tip, a door positioned inside of the elongated cylinder and configured to move between an open position to expose the therapy window and a closed position to seal the therapy window, a balloon positioned within the inner probe diameter, a cylindrical light diffuser position inside of the balloon, and a detector fiber positioned proximate the cylindrical light diffuser.

23 Claims, 6 Drawing Sheets

FIG. 9A

Providing a microprocessor; determining a total treatment dose; calculating a delivered dose of the therapy light using the detector fiber and the microprocessor; and continuing the illuminating of the cylindrical light diffuser with the therapy light until the delivered dose is substantially equal to the total treatment dose
114

Stopping the illuminating of the cylindrical light diffuser; deflating the balloon; moving the door to the closed position; and removing the probe assembly from the body of the patient
116

*FIG. 9B*

SMALL PROFILE LIGHT THERAPY PROBE

BACKGROUND

Field of the Disclosure

This application claims the benefit of Patent Cooperation Treaty Patent Application Serial No. PCT/US 22/40271 filed 13 Aug. 2022. The disclosure of the application above is incorporated herein by reference in its entirety.

Description of the Related Art

Light therapy can be used for the treatment of conditions in multiple ways. For example, light therapies involve the delivery of a therapeutic light through a fiber optic device placed proximal to or within a target tumor.

Light therapies can be combined with prior administration of light sensitizing medication (i.e., photosensitizer) that absorbs the therapeutic light and interacts with surrounding tissue constituents (e.g., oxygen) to generate reactive species that can destroy the target tissue. This form of therapy is known as photodynamic therapy ("PDT").

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In one general aspect, an optical light delivery device may include a probe assembly having an elongated cylinder having a probe inner diameter and a probe outer diameter and a probe tip positioned on a distal end, a therapy window positioned in a side portion of the elongated cylinder proximal the probe tip, a balloon positioned within the inner probe diameter, a cylindrical light diffuser position inside of the balloon, and a detector fiber positioned proximate the cylindrical light diffuser.

Implementations may include one or more of the following features. The optical light delivery device may include a door positioned inside of the elongated cylinder and configured to move between an open position to expose the therapy window and a closed position to seal the therapy window. The optical light delivery device where the probe assembly is configured to be positioned within a body of a patient adjacent to a target tissue. The optical light delivery device where the balloon is configured to be inflated to an expanded condition positioned beyond the probe outer diameter and is further configured to conformably contact the target tissue. The optical light delivery device where the cylindrical light diffuser is configured to be coupled to a light source configured to produce a therapy light. The optical light delivery device where the balloon is further configured to be inflated with a light scattering material and configured to transmit the therapy light to the target tissue. The optical light delivery device where the balloon is configured to be coupled to a pump. The optical light delivery device where the detector fiber is configured to detect the therapy light. The optical light delivery device may include a lightguide cable assembly where the cylindrical light diffuser is configured to be coupled to the light source by the lightguide cable assembly. Implementations of the described techniques may include hardware, a method or process, or a computer tangible medium.

In one general aspect, a method may include providing a probe assembly having an elongated cylinder having a probe inner diameter and a probe outer diameter and a probe tip positioned on a distal end, a therapy window positioned proximal the probe tip, a door positioned inside of the elongated cylinder and configured to move between an open position to expose the therapy window and a closed position to seal the therapy window, a balloon positioned within the inner probe diameter, a cylindrical light diffuser position inside of the balloon, and a detector fiber positioned proximate the cylindrical light diffuser. The method may also include positioning the probe assembly in a body of a patient with the therapy window proximate the target tissue. The method may furthermore include moving the door to the open position. The method may in addition include inflating the balloon with a light scattering material and positioning the balloon at least partially against the target tissue. The method may moreover include illuminating the cylindrical light diffuser with the therapy light. Other embodiments of this aspect include corresponding computer systems, apparatus, and computer programs recorded on one or more computer storage devices, each configured to perform the actions of the methods.

Implementations may include one or more of the following features. The method may include detecting the therapy light using the detector fiber. The method may include stopping the illuminating of the cylindrical light diffuser, deflating the balloon, moving the door to the closed position, and removing the probe assembly from the body of the patient. The method may include providing a microprocessor, determining a total treatment dose, calculating a delivered dose of the therapy light using the detector fiber and the microprocessor, and continuing the illuminating of the cylindrical light diffuser with the therapy light until the delivered dose is substantially equal to the total treatment dose. The method may include providing a light source to produce the therapy light and controlling the light source with the microprocessor. The method may include providing a pump in fluid communication with a reservoir and the balloon, pumping the light scattering material from the reservoir to the balloon to inflate the balloon, and pumping the light scattering material from the balloon to the reservoir to deflate the balloon. Implementations of the described techniques may include hardware, a method or process, or a computer tangible medium.

In one general aspect, a system may include a probe assembly having an elongated cylinder having a probe inner diameter and a probe outer diameter and a probe tip positioned on a distal end, a therapy window positioned in a side of the elongated cylinder proximal the probe tip, a door positioned inside of the elongated cylinder and configured to move between an open position to expose the therapy window and a closed position to seal the therapy window, a balloon positioned within the inner probe diameter, a cylindrical light diffuser position inside of the balloon, and a detector fiber positioned proximate the cylindrical light diffuser. the system may also include the probe assembly configured to be positioned in a body of a patient with the therapy window proximate the target tissue. the system may furthermore include a processor configured to move the door to the open position, inflate the balloon with a light scattering material to an expanded position beyond the probe outer diameter, and illuminate the cylindrical light diffuser with the therapy light. the system may in addition include the probe assembly configured to position the balloon at least partially against the target tissue. Other embodiments of this aspect include corresponding computer systems, apparatus, and computer programs recorded on one or more computer storage devices, each configured to perform the actions of the methods.

Implementations may include one or more of the following features. the system where the detector fiber is configured to detect the therapy light. the system where the processor is further configured to cease to illuminate the cylindrical light diffuser, deflate the balloon, and move the door to the closed position. the system where the processor is further configured to determine a total treatment dose, calculate a delivered dose of the therapy light using the detector fiber, and continue to illuminate the cylindrical light diffuser with the therapy light until the delivered dose is substantially equal to the total treatment dose. the system may include a light source configured to produce the therapy light, and where the processor is further configured to control the light source. the system may include an instrument housing the light source, the processor and an optical detector in electrical communication, and a lightguide cable assembly optically connecting the light source to the cylindrical light diffuser and optically connecting the optical detector to the detector fiber. the system where the optical detector may include a photodiode configured to produce a current signal based on a light intensity received from the detector fiber. the system where the current signal is used to calculate the delivered dose. the system may include a pump in fluid communication with a reservoir and the balloon, and where the pump is configured to pump the light scattering material from the reservoir to the balloon to inflate the balloon, and pump the light scattering material from the balloon to the reservoir to deflate the balloon. Implementations of the described techniques may include hardware, a method or process, or a computer tangible medium.

BRIEF DESCRIPTION OF THE DRAWINGS

FIG. 9B is a continuation of the process flow diagram of FIG. 9A, according to an example of the present disclosure.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

The present disclosure relates to an optical light therapy application and monitoring system which can be configured to optimized for a particular PDT procedure and can produce a known and controllable dosimetry. Such a system is useful in the treatment of cancerous tumors as well as residual abnormal tissue following surgical resection of a tumor. The PDT procedure can be used as adjuvant therapy to kill of any residual amounts of abnormal tissue left behind. In addition, the PDT treatment can be used to enhance a response to immuno-therapy treatments. It should be appreciated that the therapy type can be selected from the group that may include necrotic, apoptotic, vascular and immunogenicity. The present disclosure includes a customizable optical surface applicator (optical surface applicator) and an optical surface applicator signal monitoring system.

Figure 1:
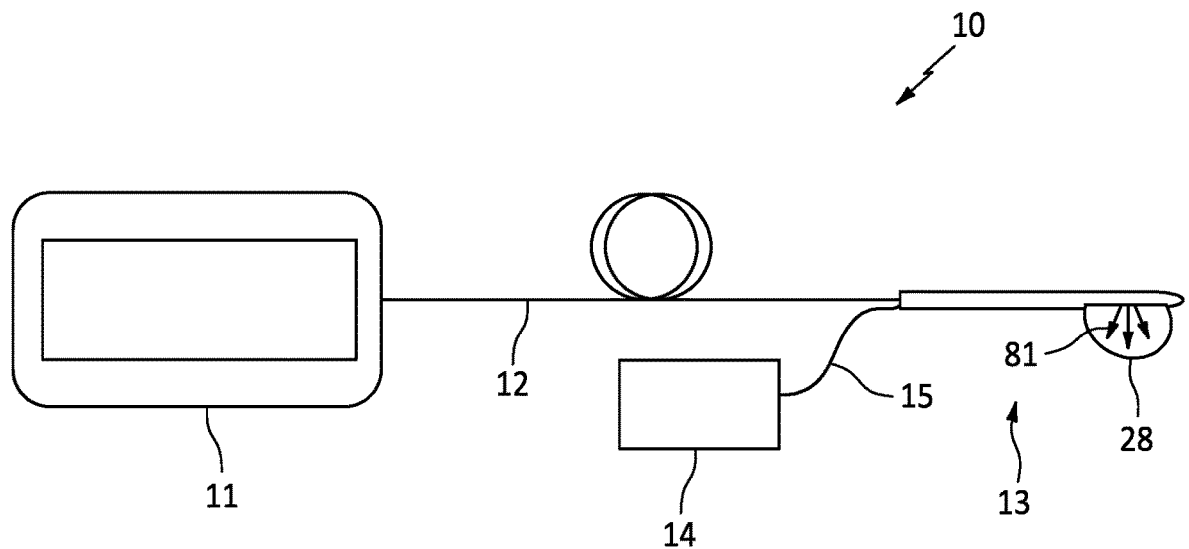
FIG. 1 is a schematic diagram of a PDT delivery system, according to an example of the present disclosure.

Referring to FIG. 1 there is shown a schematic of an implementation of a PDT system 10 in accordance with the present disclosure. PDT system 10 comprises instrument 11, lightguide cable assembly 12, pumping unit 14, hose 15 and probe assembly 13. Instrument 11 can include a light source such as a laser, a graphical user interface (GUI), a processor, a power module, an optical detector, fiber connector, and various electrical and optical interfaces. The laser, the graphical user interface (GUI), the processor, the power module, the optical detector can all be in electrical communication. The GUI can include a touch screen configured to allow a user to input data and read various operating parameter as will be disclosed in more detail herein after.

Figure 2:
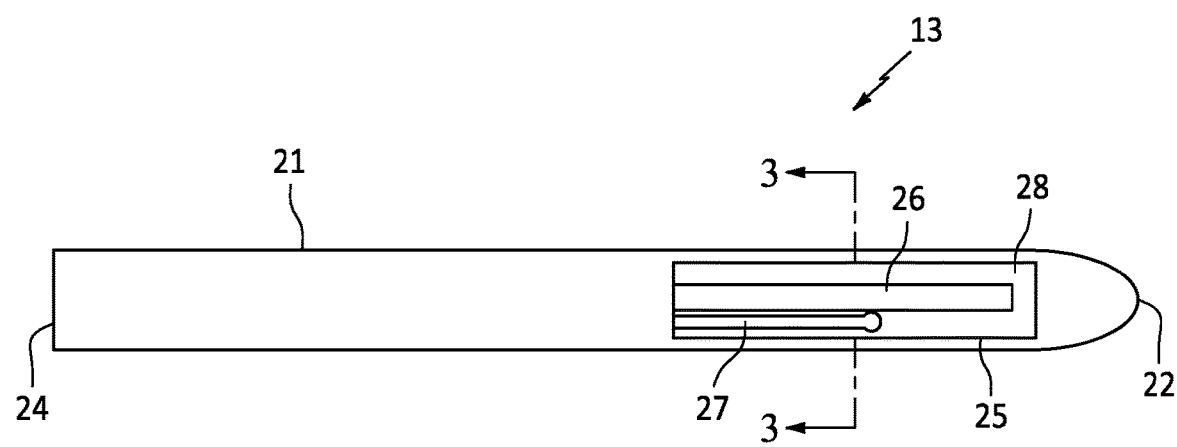
FIG. 2 is a top view of a probe assembly, according to an example of the present disclosure.

The laser can be a continuously operated (continuous wave or CW) laser operated at a predetermined constant power (i.e. not pulsed). The laser can be selected for output power up to about 2 watts. The actual operating power can depend on various parameters, such as the treated area, dosage and irradiance as will be disclosed in more detail herein after. The laser can be selected to produce therapy light at a wave wavelength that matches a selected photosensitizing agent. The PDT system 10 can be used to administer a prescribed light dose rate (mW/cm$^2$) and total fluence dose (J/cm2) for the photo-activation of a photosensitizer agent for an adjuvant treatment following malignant tumor surgical resection in the thoracic cavity for loco-regional disease control in the surgical bed or as a treatment to stimulate host tumor response and alter the host tumor microenvironment and immunosuppression in patients with lung cancer with pleural disease. For instance, the laser can be selected to operate at a wavelength of about 630 nm when used to activate the photosensitizing agent comprised of porfimer sodium. The processor can include memory configured to store software for the operation of the laser, power module, GUI and to perform various calibrations, measurements, and calculations. The optical detector can comprise a photodiode and amplifier providing a current signal based on light intensity received from therapy light detector 27 (FIG. 2). The current signal is provided to the processor and using an appropriate algorithm can derive accurate absolute dose rate (mW/cm2) and total dose (J/cm2) values during use.

Lightguide cable assembly 12 can include a pair of optical fibers positioned within sheath comprised of a medical grade silicone material. The optical fibers are selected to transmit therapy light from the instrument to an optical light delivery device such as probe 13 and to transmit detected light from the probe to the instrument. The ends of the optical fibers are terminated with appropriate connectors to topically couple lightguide cable to instrument 11 and probe 13 such as subminiature version A (SMA) connectors. Lightguide cable assembly 12 can also comprise other components such as additional optical fibers and electrical conductors and the like. Pumping unit 14 can include a pump and a reservoir and is in fluid communication with probe assembly 13 via hose 15. The reservoir is configured to hold a light scattering liquid, such as saline, and the pump is configured to pump the light scattering liquid into and out of the probe assembly as will disclosed in more detail herein after. Pumping unit 14 can be electrically coupled to instrument 11 and the processor can control the operation of the pump.

Figure 3:
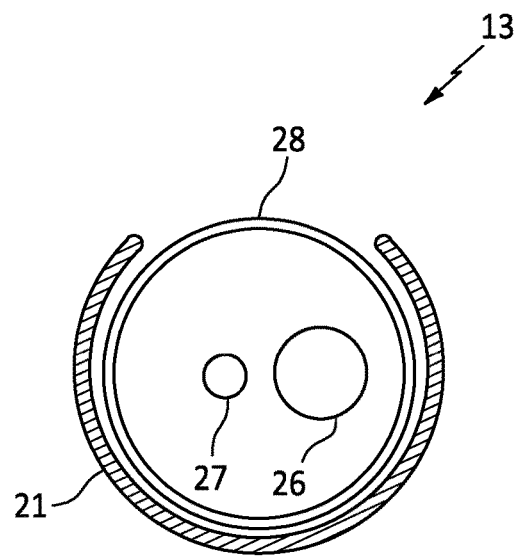
FIG. 3 is a cross-sectional view of a probe assembly, according to an example of the present disclosure.

With further reference to FIGS. 2, 3, there is shown probe assembly 13 in accordance with implementations of the current disclosure. FIG. 2 is a front view of probe assembly 13 and FIG. 3 is cross section of probe assembly 13 taken substantially along cut line 3-3 if FIG. 2. Probe assembly 13 can be comprised of any suitable material and includes a probe body comprised an elongated cylindrical body 21 having a conical probe tip 22 positioned at a distal end, a sealable open end 24 positioned at a proximal end, and a treatment window 25 positioned in a side portion near the distal end. In some implementations, elongated cylindrical body 21 can have a small outside diameter, on the order of about 3.5 mm or less, and can have an over length of about 700 mm. Probe assembly further comprises a therapy light emitter 26, a therapy light detector 27 and a balloon 28. Balloon 28 includes an open end and is disposed within an inside diameter of the probe body of the hollow portion of elongated cylindrical body 21 with the open end positioned at sealable open end 24. Balloon 28 is sized to fit within the inside diameter in a deflated condition and is selected from medical grade materials having adequate elongation properties of 100-800% to accommodate for an inflated condition during operation as will be disclosed in more detail herein after. Balloon 28 is hydraulically connected to pumping unit 14 via hose 15 coupled to the open end of the balloon. Therapy light emitter 26 can comprise a cylindrical light diffuser having a 50 mm outside diameter such as an RD50 commercially available from Medlight, SA. Therapy light emitter 26 is positioned within the inside of balloon 28 and is optically coupled the laser of instrument 11 via lightguide cable 12 to deliver treatment light to a target tissue of patient as will be disclosed herein after. Therapy light detector 27 can comprise a fiber isotropic detector such as IP85 commercially available from Medlight, SA. Therapy light detector 27 is positioned within the inside of balloon 28 proximate therapy light emitter 26 and is optically coupled the detector of instrument 11 via lightguide cable 12.

Figure 4:
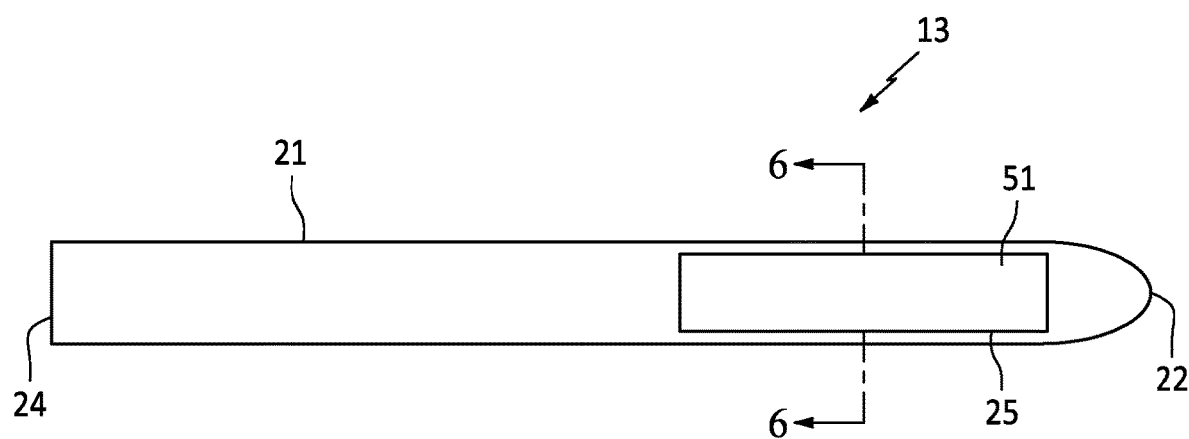
FIG. 4 is a top view of a probe assembly showing a door in a fully closed position, according to an example of the present disclosure.
Figure 5:
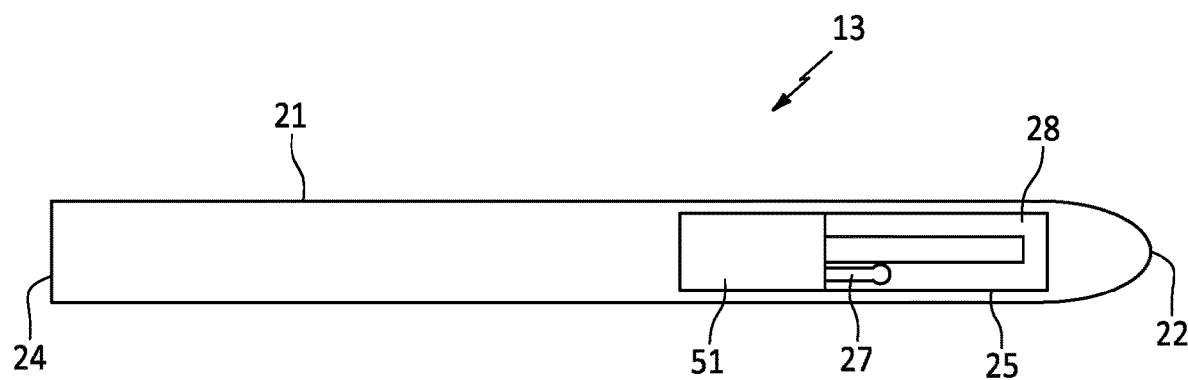
FIG. 5 is a top view of a probe assembly showing a door in a partially closed position, according to an example of the present disclosure.
Figure 6:
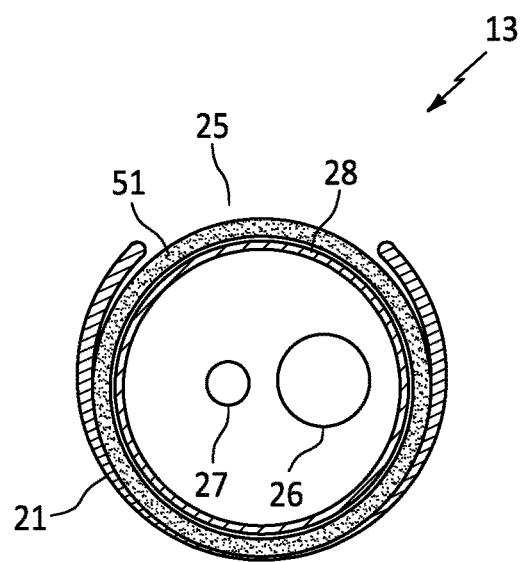
FIG. 6 is a cross-sectional view of a probe assembly showing a door in a fully closed position, according to an example of the present disclosure.

FIG. 4 is a front view of probe assembly 13 including door 51 in a closed position and FIG. 5 is a front view of probe assembly 13 including door 51 in a partially closed position. It should be noted for clarity that FIG. 2 can be a front view of probe assembly 13 including door 51 in an open position. FIG. 6 is a cross section taken substantially along cut line 6-6 of FIG. 5. In these various figures, door 51 is tubular in shape and is sized to fit within an inner diameter of the probe body of elongated cylindrical body 21 and is tubular in shape and slidably positioned therein between a fully opened position (FIG. 2) and a fully closed position and is incrementally adjustable at positions therebetween. Balloon 28, as well as therapy light emitter 26 and therapy light detector are positioned within the door in the closed position. It should be noted by those skilled in the art that door 51 provide inventive advantages over PDT probes of the prior art. In operation, probe assembly 13 can be manipulated and inserted into a body of patient without inadvertently exposing an operator, a person in in proximity or a patient with therapy light while door 51 is closed. In addition, with door 51 in the closed position the probe body of probe assembly 13 presents as a smoother shape by covering therapy window 25 allowing the probe to be inserted interstitially without catching on the tissue of the patient. Further, door 51 contains balloon 28 in the closed position and can assist in the deflating of the balloon in the post procedure sequence as will be disclosed in more detail herein after. Door 51 can be moved from the various positions using a mechanism incorporated into or remote to probe assembly 13 such as an actuation rod (not shown) coupled to the door. The manipulation of the actuation rod can be performed manually by an operator or powered by a device controlled by the processor within instrument 11.

Figure 7:
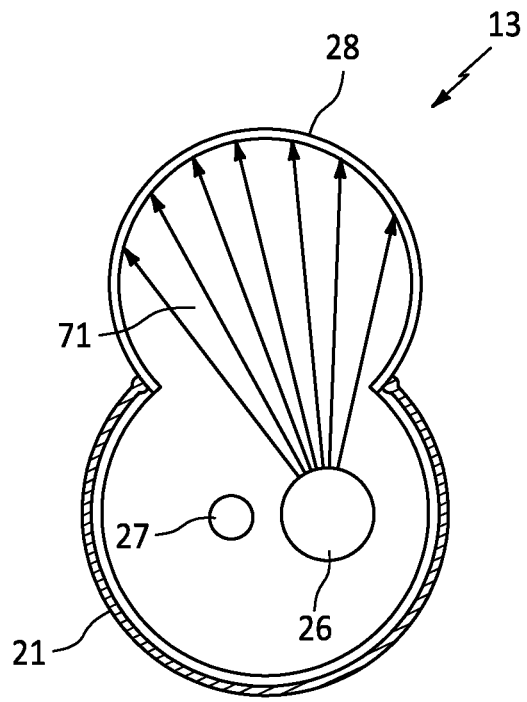
FIG. 7 is a cross-sectional view of a probe assembly showing a balloon in an expanded condition, according to an example of the present disclosure.
Figure 8:
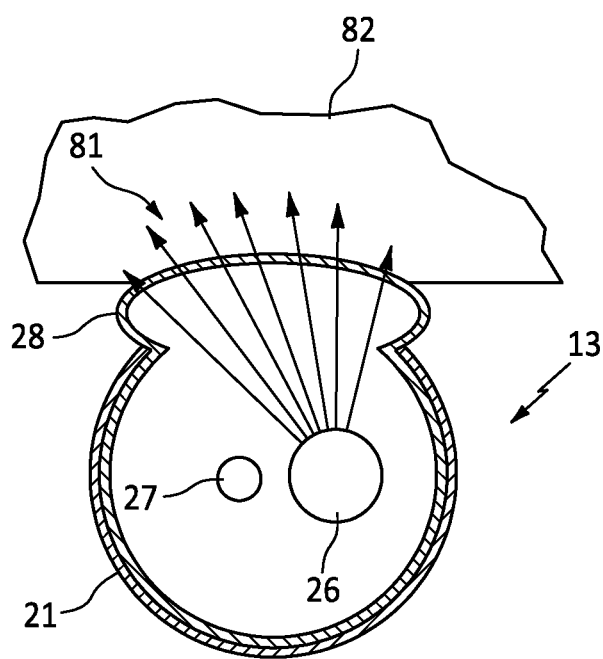
FIG. 8 is a cross-sectional view of a probe assembly showing a balloon in an expanded condition positioned against a target tissue, according to an example of the present disclosure.

Referring now to FIG. 7 there is shown the same cross section of probe assembly 13 as shown in FIG. 6 with door 51 in the fully open position and with balloon 8 in the inflated condition. With further reference back to FIG. 1, in this implementation of PDT system 10, a light scattering solution can be pumped into balloon 28 by pumping system 14 to expand the balloon into the inflated condition. In so doing, balloon 28 expands through treatment window 25 and provides a scattering medium for spreading therapy light 71 emitted from therapy light emitter 26 into a uniform irradiance pattern. It should be appreciated by those skilled in the art that balloon 28 is shown in a fully expanded position with the biasing force being the elasticity of the balloon material. In practice, and now with reference to FIG. 8, probe assembly 13 can be configured to be positioned adjacent or proximate to a target tissue 82 of a patient and when balloon 28 is placed against the target tissue the balloon will conform to the surface of the target tissue and provide an efficient means for delivering the irradiance pattern 81 of therapy light 71. In operation, probe assembly 13 is manipulated to the target tissue 82 either manually by trained medical personnel using imaging of the target area or robotically using digital information about the location and position of the target area. In some cases the conical probe tip 22 of probe assembly 13 can pierce the target tissue 82 of a patient and the therapy can be delivered interstitially. Treatment window 25 is moved to at least a partially open position and light scattering liquid is pumped into balloon 28 using pumping system 15. Instrument 11 is energized, and the laser delivers therapy light 71 to light emitter 26. Balloon 28 and the light scattering liquid produce a uniform irradiance pattern 81 of the therapy light 71. The process of delivering therapy light 71 to the target tissue is continued until the delivered dose of therapy light is substantially equal to the total treatment dose. As will be disclosed in more detail herein after, once the treatment is complete, the laser is de-energized, balloon 28 can be deflated by pumping the light scattering liquid from the balloon using pumping system 15. Subsequent to the deflating of balloon 28, door 51 can be moved to the fully closed position and probe assembly 13 can be removed from the body of the patient or moved to a secondary target tissue location for further treatment.

Figure 9A:
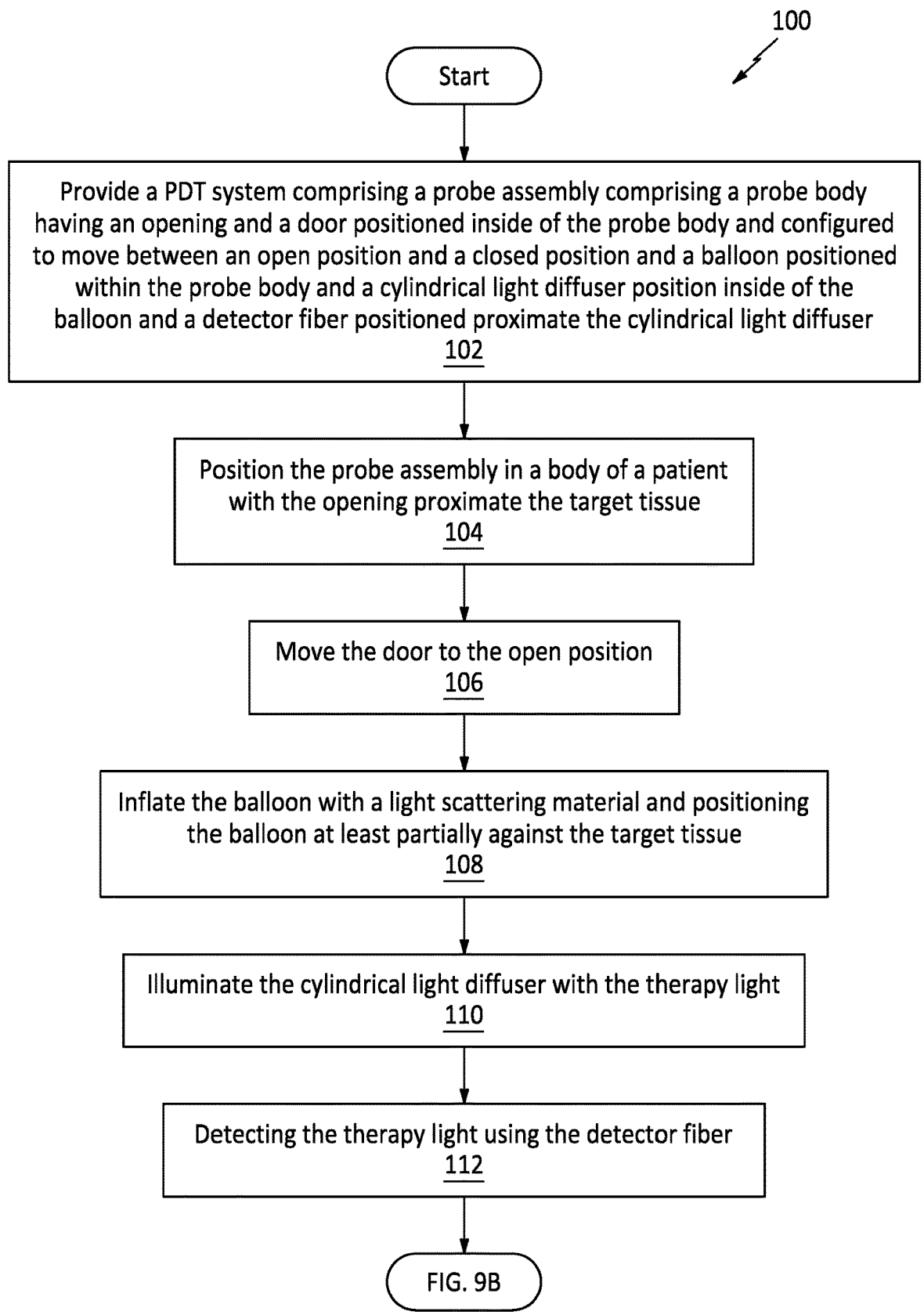
FIG. 9A is a process flow diagram of a method of delivering therapy light to a target area of a patient, according to an example of the present disclosure.

FIG. 9 is a flowchart of an example method 100 of delivering therapy light to a target area of a patient. In some implementations, one or more process blocks of FIG. 9 may be performed by using implementations of PDT system 10 (FIG. 1) of the present disclosure.

As shown in FIG. 9, process 100 may include providing a probe assembly having a probe body having a probe tip positioned on a distal end, an opening positioned proximal the probe tip, a door positioned inside of the elongated cylinder and configured to move between an open position to expose the opening and a closed position to seal the opening, a balloon positioned within the inner probe diameter, a cylindrical light diffuser position inside of the balloon, and a detector fiber positioned proximate the cylindrical light diffuser (block 102). As also shown in FIG. 9, process 100 may include positioning the probe assembly in a body of a patient with the opening proximate the target tissue (block 104). As further shown in FIG. 9, process 100 may include moving the door to the open position (block 106). As also shown in FIG. 9, process 100 may include inflating the balloon with a light scattering material and positioning the balloon at least partially against the target tissue (block 108). As further shown in FIG. 9, process 100 may include illuminating the cylindrical light diffuser with the therapy light (block 110).

Process 100 may include additional implementations, such as any single implementation or any combination of implementations described below and/or in connection with one or more other processes described elsewhere herein. In a first implementation, the method of delivering therapy light may include detecting the therapy light using the detector fiber (block 112).

In furtherance of process 100, the method of delivering therapy light further includes providing a microprocessor, determining a total treatment dose, calculating a delivered dose of the therapy light using the detector fiber and the microprocessor, and continuing the illuminating of the cylindrical light diffuser with the therapy light until the delivered dose is substantially equal to the total treatment dose (block 114).

In furtherance of process 100, the method of delivering therapy light further includes stopping the illuminating of the cylindrical light diffuser, deflating the balloon, moving the door to the closed position, and removing the probe assembly from the body of the patient (block 116).

Although FIG. 9 shows example blocks of process 100, in some implementations, process 100 may include additional blocks, fewer blocks, different blocks, or differently arranged blocks than those depicted in FIG. 9. Additionally, or alternatively, two or more of the blocks of process 100 may be performed in parallel.

The foregoing disclosure provides illustration and description but is not intended to be exhaustive or to limit the implementations to the precise form disclosed. Modifications may be made in light of the above disclosure or may be acquired from practice of the implementations. As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein. As used herein, satisfying a threshold may, depending on the context, refer to a value being greater than the threshold, greater than or equal to the threshold, less than the threshold, less than or equal to the threshold, equal to the threshold, and/or the like, depending on the context. Although particular combinations of features are recited in the claims and/or disclosed in the specification, these combinations are not intended to limit the disclosure of various implementations. In fact, many of these features may be combined in ways not specifically recited in the claims and/or disclosed in the specification.

Although each dependent claim listed below may directly depend on only one claim, the disclosure of various implementations includes each dependent claim in combination with every other claim in the claim set. No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. An optical light delivery device comprising;
   a probe assembly comprising;
      an elongated cylinder having a probe inner diameter and a probe outer diameter and a probe tip positioned on a distal end;
      a therapy window positioned in a side portion of the elongated cylinder proximal the probe tip;
      a balloon positioned within the inner probe diameter;
      a cylindrical light diffuser position inside of the balloon;
      a detector fiber positioned proximate the cylindrical light diffuser; and
      a door positioned inside of the elongated cylinder and configured to move between an open position to expose the therapy window and a closed position to seal the therapy window.

2. The optical light delivery device of claim 1 wherein the probe assembly is configured to be positioned within a body of a patient adjacent to a target tissue.

3. The optical light delivery device of claim 2, wherein the balloon is configured to be inflated to an expanded condition positioned beyond the probe outer diameter with the door in the open position and wherein the balloon is further configured to conformably contact the target tissue.

4. The optical light delivery device of claim 3, wherein the cylindrical light diffuser is configured to be coupled to a light source configured to produce a therapy light.

5. The optical light delivery device of claim 4, wherein the balloon is further configured to be inflated with a light scattering material and configured to transmit the therapy light to the target tissue.

6. The optical light delivery device of claim 5 wherein the balloon is configured to be coupled to a pump.

7. The optical light delivery device of claim 4, wherein the detector fiber is configured to detect the therapy light.

8. The optical light delivery device of claim 4 further comprising a lightguide cable assembly wherein the cylindrical light diffuser is configured to be coupled to the light source by the lightguide cable assembly.

9. A method of delivering therapy light to a target tissue comprising:
   providing a probe assembly comprising:
      an elongated cylinder having a probe inner diameter and a probe outer diameter and a probe tip positioned on a distal end;
      a therapy window positioned proximal the probe tip;
      a door positioned inside of the elongated cylinder and configured to move between an open position to expose the therapy window and a closed position to seal the therapy window;
      a balloon positioned within the inner probe diameter;
      a cylindrical light diffuser position inside of the balloon; and
      a detector fiber positioned proximate the cylindrical light diffuser;
   positioning the probe assembly in a body of a patient with the therapy window proximate the target tissue;
   moving the door to the open position;
   inflating the balloon with a light scattering material and positioning the balloon at least partially against the target tissue; and
   illuminating the cylindrical light diffuser with the therapy light.

10. The method of delivering therapy light of claim 9 further comprising detecting the therapy light using the detector fiber.

11. The method of delivering therapy light of claim 10 further comprising:
   stopping the illuminating of the cylindrical light diffuser;
   deflating the balloon;
   moving the door to the closed position; and
   removing the probe assembly from the body of the patient.

12. The method of delivering therapy light of claim 11 further comprising:
   providing a microprocessor;
      determining a total treatment dose;
      calculating a delivered dose of the therapy light using the detector fiber and the microprocessor; and
      continuing the illuminating of the cylindrical light diffuser with the therapy light until the delivered dose is equal to the total treatment dose.

13. The method of delivering therapy light of claim 12 further comprising:
   providing a light source to produce the therapy light and controlling the light source with the microprocessor.

14. The method of delivering therapy light of claim 12 further comprising:
   providing a pump in fluid communication with a reservoir and the balloon;
   pumping the light scattering material from the reservoir to the balloon to inflate the balloon; and
   pumping the light scattering material from the balloon to the reservoir to deflate the balloon.

15. A system for delivering therapy light to a target tissue comprising:
   a probe assembly comprising:
      an elongated cylinder having a probe inner diameter and a probe outer diameter and a probe tip positioned on a distal end;
      a therapy window positioned in a side of the elongated cylinder proximal the probe tip;
      a door positioned inside of the elongated cylinder and configured to move between an open position to expose the therapy window and a closed position to seal the therapy window;
      a balloon positioned within the inner probe diameter;
      a cylindrical light diffuser position inside of the balloon; and
         a detector fiber positioned proximate the cylindrical light diffuser;
      the probe assembly configured to be positioned in a body of a patient with the therapy window proximate the target tissue;
   a processor configured to:
      move the door to the open position;
      inflate the balloon with a light scattering material to an expanded position beyond the probe outer diameter; and
      illuminate the cylindrical light diffuser with the therapy light, and the probe assembly configured to position the balloon at least partially against the target tissue.

16. The system of claim 15, wherein the detector fiber is configured to detect the therapy light.

17. The system of claim 16, wherein the processor is further configured to
   cease to illuminate the cylindrical light diffuser;
   deflate the balloon; and
   move the door to the closed position.

18. The system of claim 17, wherein the processor is further configured to: determine a total treatment dose;
   calculate a delivered dose of the therapy light using the detector fiber; and
      continue to illuminate the cylindrical light diffuser with the therapy light until the delivered dose is substantially equal to the total treatment dose.

19. The system of claim 18, further comprising:
   a pump in fluid communication with a reservoir and the balloon; and
   wherein the pump is configured to:
      pump the light scattering material from the reservoir to the balloon to inflate the balloon; and
      pump the light scattering material from the balloon to the reservoir to deflate the balloon.

20. The system of claim 18, further comprising:
   a light source configured to produce the therapy light; and
   wherein the processor is further configured to control the light source.

21. The system of claim 20, further comprising:
   an instrument housing the light source, the processor and an optical detector all in electrical communication; and
   a lightguide cable assembly optically connecting the light source to the cylindrical light diffuser and optically connecting the optical detector to the detector fiber.

22. The system of claim 21, wherein the optical detector comprises a photodiode configured to produce a current signal based on a light intensity received from the detector fiber.

23. The system of claim 22, wherein the current signal is used to calculate the delivered dose.

* * * * *